US012655400B2

(12) United States Patent
Chen et al.

(10) Patent No.: US 12,655,400 B2
(45) Date of Patent: Jun. 16, 2026

(54) ENGINEERED DNA POLYMERASE WITH INCREASED PROPERTY FOR SINGLE MOLECULE SEQUENCING

(71) Applicant: Personal Genomics Taiwan, Inc., Hsinchu County (TW)

(72) Inventors: Dalton Chen, New Taipei City (TW); Ya-Chen Chen, Hsinchu County (TW); Yu-Husan Lin, Hsinchu City (TW); Yi-Ting Chou, Hsinchu City (TW); Ting-Yueh Tsai, Hsinchu City (TW); Chi-Fu Yen, New Taipei City (TW); Chao-Chi Pan, Hsinchu City (TW)

(73) Assignee: Personal Genomics Taiwan, Inc., Hsinchu County (TW)

( * ) Notice: Subject to any disclaimer, the term of this patent is extended or adjusted under 35 U.S.C. 154(b) by 283 days.

(21) Appl. No.: 18/408,593

(22) Filed: Jan. 10, 2024

(65) Prior Publication Data

US 2024/0309340 A1 Sep. 19, 2024

Related U.S. Application Data

(60) Provisional application No. 63/452,705, filed on Mar. 17, 2023.

(51) Int. Cl.
*C12N 9/12* (2006.01)

(52) U.S. Cl.
CPC .... *C12N 9/1252* (2013.01); *C12Y 207/07007* (2013.01)

(58) Field of Classification Search
CPC ...................... C12N 9/1252; C12Y 207/07007
See application file for complete search history.

(56) References Cited

U.S. PATENT DOCUMENTS

| | | | | |
|---|---|---|---|---|
| 8,906,660 | B2 * | 12/2014 | Kamtekar | ...... C12Y 207/07007 435/194 |
| 9,873,911 | B2 | 1/2018 | Kamtekar et al. | |
| 9,885,025 | B2 * | 2/2018 | Skirgaila | .............. C12N 9/1252 |
| 11,155,860 | B2 * | 10/2021 | White | .................. C12Q 1/6869 |
| 2010/0112645 | A1 | 5/2010 | Clark et al. | |
| 2014/0094375 | A1 | 4/2014 | Kamtekar et al. | |

FOREIGN PATENT DOCUMENTS

| | | |
|---|---|---|
| EP | 2813576 | 6/2016 |

OTHER PUBLICATIONS

Banerjee et al., Improving enzymes for biomass conversion: A basic research perspective. Bioenerg. Res., 2010, vol. 3: 82-92. (Year: 2010).*
Broun et al., Catalytic plasticity of fatty acid modification enzymes underlying chemical diversity of plant lipids. Science, 1998, vol. 282: 1315-1317. (Year: 1998).*
Chica et al., Semi-rational approaches to engineering enzyme activity: combining the benefits of directed evolution and rational design. Curr. Opi. Biotechnol., 2005, vol. 16: 378-384. (Year: 2005).*
Devos et al., Practical limits of function prediction. Proteins: Structure, Function, and Genetics. 2000, vol. 41: 98-107. (Year: 2000).*
Kisselev L., Polypeptide release factors in prokaryotes and eukaryotes: same function, different structure. Structure, 2002, vol. 10: 8-9. (Year: 2002).*
Seffernick et al., Melamine deaminase and Atrazine chlorohydrolase: 98 percent identical but functionally different. J. Bacteriol., 2001, vol. 183 (8): 2405-2410. (Year: 2001).*
Sen et al., Developments in directed evolution for enzyme functions. Appl. Biochem. Biotechnol., 2007, vol. 143: 212-223. (Year: 2007).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Jing Wu et al., "DNA binding strength increases the processivity and activity of a Y-Family DNA polymerase", Scientific Reports, Jul. 6, 2017, pp. 1-12, vol. 7, No. 4756.
Miguel De Vega et al., "Improvement of φ29 DNA polymerase amplification performance by fusion of DNA binding motifs", PNAS, Sep. 21, 2010, pp. 16506-16511, vol. 107, No. 38.
Seaim Lwin Aye et al, "Engineering of DNA polymerase I from Thermus thermophilus using compartmentalized self-replication", Biochemical and Biophysical Research Communications, Mar. 2018, pp. 170-176.
Yaping Gao et al, "Chimeric Phi29 DNA polymerase with helix-hairpin-helix motifs shows enhanced salt tolerance and replication performance", Microbial Biotechnology, May 2021, pp. 1642-1656.
Tadas Povilaitis et al, "In vitro evolution of phi29 DNA polymerase using isothermal compartmentalized self replication technique", Protein Engineering, Design & Selection, Sep. 2016, pp. 617-628.
"Office Action of Taiwan Counterpart Application", issued on Aug. 26, 2024, pp. 1-11.

* cited by examiner

*Primary Examiner* — Ganapathirama Raghu
(74) *Attorney, Agent, or Firm* — JCIPRNET

(57) ABSTRACT

An engineered DNA polymerase, with increased property for single molecule sequencing compared to a wild-type DNA polymerase, comprising a combination of mutation sites and functional domains, wherein the combination of mutation sites and functional domains includes thermostable mutation sites, low Kd mutation sites, exonuclease-deficient sites and DNA binding domains.

1 Claim, 2 Drawing Sheets

Specification includes a Sequence Listing.

```
                           SEQUENCE LISTING

Sequence total quantity: 4
SEQ ID NO: 1              moltype = AA   length = 708
FEATURE                  Location/Qualifiers
source                   1..708
                         mol_type = protein
                         organism = synthetic construct
SEQUENCE: 1
MGSSSSGLND IFEAQKIEWH EGASSHHHHH HSSGLVPRGS HMKHMPRKRY SCDFETTTKV  60
EDCRVWAYGY MNIEDHSEYK IGNSLDEFMA WALKVQADLY FHNLKFDGAF IINWLERNGF  120
KWSADGLPNT YNTIISRTGQ WYMIDICLGY KGKRKIHTVI YDSLKKLPFP VKKIAKDFKL  180
TVLDGDIDYH KERPVGYKIT PEEYAYIKND IQIIAEALLI QFKQGLDRMT AGSDSLKDFK  240
DIITTKKFKK VFPTLSLGLD KKVRKAYRGG FTWLNDRFKG KEIGEGMVFD INSAYPAQMY  300
SRLLPYGEPI VFEGKYVWDE DYPLHIQHIR CEFELKEGYI PTIQIKRSRF YKGNEYLKSS  360
GGEIADLWLS NVDLELMKEH YDLYNVEYIS GLKFKATTGL FKDFIDKWTY IKTTSYGAIK  420
QLAKLMLNSL YGKFASNPDV TGKVPYLKEN GALGFRLGEE ETKDPVYTPM GVFITAWGRY  480
TTITAAQACY DRIIYCDTDS IHLTGTEIPD VIKDIVDPKK LGYWEHESTF KRAKYLRQKT  540
YIQDIYMKRV KGYLVQGSPD DYTDIKFSVK CAGMTDKIKK EVTFENFKVG FSRKMKPKPV  600
QVPGGVVLVD MTFTIKGGGS GGGSGGGSGH HHHHHHHHHG TGSGAATVKF KYKGEEKEVD  660
ISKIKKVWRV GKMISFTYDE GGGKTGRGAV SEKDAPKELL QMLEKQKK              708

SEQ ID NO: 2              moltype = AA   length = 708
FEATURE                  Location/Qualifiers
source                   1..708
                         mol_type = protein
                         organism = synthetic construct
SEQUENCE: 2
MGSSSSGLND IFEAQKIEWH EGASSHHHHH HSSGLVPRGS HMKHMPRKRY SCDFETTTKV  60
EDCRVWAYGY MNIEDHSEYK IGNSLDEFMA WALKVQADLY FHNLKFDGAF IINWLERNGF  120
KWSADGLPNT YNTIISRTGQ WYMIDICLGY KGKRKIHTVI YDSLKKLPFP VKKIAKDFKL  180
TVLKGDIDLH KERPVGYKIT PEEYAYIKND IQIIAEALLI QFKQGLDRMT AGSDSLKDFK  240
DIITTKKFKK VFPTLSLGLD KKVRKAYRGG FTWLNDRFKG KEIGEGMVFD INSAYPAQMY  300
SRLLPYGEPI VFEGKYVWDE DYPLHIQHIR CEFELKEGYI PTIQIKRSRF YKGNEYLKSS  360
GGEIADLWLS NVDLELMKEH YDLYNVEYIS GLKFKATTGL FKDFIDKWTY IKTTSYGAIK  420
QLAKLMLNSL YGKFASNPDV TGKVPYLKEN GALGFRLGEE ETKDPVYTPM GVFITAWGRY  480
TTITAAQACY DRIIYCDTDS IHLTGTEIPD VIKDIVDPKK LGYWEHESTF KRAKYLRQKT  540
YIQDIYMKRV KGYLVQGSPD DYTDIKFSVK CAGMTDKIKK EVTFENFKVG FSRKMKPKPV  600
QVPGGVVLVD MTFTIKGGGS GGGSGGGSGH HHHHHHHHHG TGSGAATVKF KYKGEEKEVD  660
ISKIKKVWRV GKMISFTYDE GGGKTGRGAV SEKDAPKELL QMLEKQKK              708

SEQ ID NO: 3              moltype = AA   length = 708
FEATURE                  Location/Qualifiers
source                   1..708
                         mol_type = protein
                         organism = synthetic construct
SEQUENCE: 3
MGSSSSGLND IFEAQKIEWH EGASSHHHHH HSSGLVPRGS HMKHMPRKRY SCDFETTTKV  60
EDCRVWAYGY MNIEDHSEYK IGNSLDEFMA WALKVQADLY FHNLKFDGAF IINWLERNGF  120
KWSADGLPNT YNTIISRTGQ WYMIDICLGY KGKRKIHTVI YDSLKKLPFP VKKIAKDFKL  180
TVLAGDIDYH KERPVGYKIT PEEYAYIKND IQIIAEALLI QFKQGLDRMT AGSDSLKDFK  240
DIITTKKFKK VFPTLSLGLD KKVRKAYRGG FTWLNDRFKG KEIGEGMVFD INSAYPAQMY  300
SRLLPYGEPI VFEGKYVWDE DYPLHIQHIR CEFELKEGYI PTIQIKRSRF YKGNEYLKSS  360
GGEIADLWLS NVDLELMKEH YDLYNVEYIS GLKFKATTGL FKDFIDKWTY IKTTSYGAIK  420
QLAKLMLNSL YGKFASNPDV TGKVPYLKEN GALGFRLGEE ETKDPVYTPM GVFITAWGRY  480
TTITAAQACY DRIIYCDTDS IHLTGTEIPD VIKDIVDPKK LGYWEHESTF KRAKYLRQKT  540
YIQDIYMKRV KGYLVQGSPD DYTDIKFSVK CAGMTDKIKK EVTFENFKVG FSRKMKPKPV  600
QVPGGVVLVD MTFTIKGGGS GGGSGGGSGH HHHHHHHHHG TGSGAATVKF KYKGEEKEVD  660
ISKIKKVWRV GKMISFTYDE GGGKTGRGAV SEKDAPKELL QMLEKQKK              708

SEQ ID NO: 4              moltype = AA   length = 708
FEATURE                  Location/Qualifiers
source                   1..708
                         mol_type = protein
                         organism = synthetic construct
SEQUENCE: 4
MGSSSSGLND IFEAQKIEWH EGASSHHHHH HSSGLVPRGS HMKHMPRKRY SCDFETTTKV  60
```

-continued

```
EDCRVWAYGY MNIEDHSEYK IGNSLDEFMA WALKVQADLY FHNLKFDGAF IINWLERNGF  120
KWSADGLPNT YNTIISRTGQ WYMIDICLGY KGKRKIHTVI YDSLKKLPFP VKKIAKDFKL  180
TVLSGDIDYH KERPVGYKIT PEEYAYIKND IQIIAEALLI QFKQGLDRMT AGSDSLKDFK  240
DIITTKKFKK VFPTLSLGLD KKVRKAYRGG FTWLNDRFKG KEIGEGMVFD INSAYPAQMY  300
SRLLPYGEPI VFEGKYVWDE DYPLHIQHIR CEFELKEGYI PTIQIKRSRF YKGNEYLKSS  360
GGEIADLWLS NVDLELMKEH YDLYNVEYIS GLKFKATTGL FKDFIDKWTY IKTTSYGAIK  420
QLAKLMLNSL YGKFASNPDV TGKVPYLKEN GALGFRLGEE ETKDPVYTPM GVFITAWGRY  480
TTITAAQACY DRIIYCDTDS IHLTGTEIPD VIKDIVDPKK LGYWEHESTF KRAKYLRQKT  540
YIQDIYMKRV KGYLVQGSPD DYTDIKFSVK CAGMTDKIKK EVTFENFKVG FSRKMKPKPV  600
QVPGGVVLVD MTFTIKGGGS GGGSGGGSGH HHHHHHHHHG TGSGAATVKF KYKGEEKEVD  660
ISKIKKVWRV GKMISFTYDE GGGKTGRGAV SEKDAPKELL QMLEKQKK              708
```

ENGINEERED DNA POLYMERASE WITH INCREASED PROPERTY FOR SINGLE MOLECULE SEQUENCING

CROSS-REFERENCE TO RELATED APPLICATION

This application claims the priority benefits of U.S. provisional application Ser. No. 63/452,705, filed on Mar. 17, 2023. The entirety of the above-mentioned patent application is hereby incorporated by reference herein and made a part of this specification.

REFERENCE TO A SEQUENCE LISTING

The instant application contains a Sequencing Listing which has been submitted electronically in XML file and is hereby incorporated by reference in its entirety. Said XML copy, created on Sep. 28, 2023, is named 132424-US-sequence listing and is 7,157 bytes in size.

BACKGROUND

Technical Field

The invention relates to an engineered DNA polymerase, and more particularly, to an engineered DNA polymerase with increased property for single molecule sequencing.

Description of Related Art

DNA polymerases play an important role in many applications, such as nucleic acid sequencing, nucleic acid amplification, cloning, protein engineering, diagnostics, molecular medicine, and many other technologies. In the application for single molecule sequencing, the requirement for a good DNA polymerase includes: High affinity to nucleotide analog, reduced exonuclease activity, increased processivity (enhance DNA binding stability), protein thermostability, accuracy, read length and etc. DNA polymerases replicate the genomes of living organisms. In addition to this central role in biology, DNA polymerases are also ubiquitous tools of biotechnology.

In recent years, DNA polymerase mutants have been identified that have a variety of useful properties. Additional modified polymerases, e.g., modified polymerases that display improved properties useful for single molecule sequencing (SMS) and other polymerase applications (e.g., DNA amplification, sequencing, labeling, detection, cloning, etc.), are desirable.

SUMMARY

The invention provides an engineered DNA polymerase, with increased property for single molecule sequencing compared to a wild-type DNA polymerase, comprising a combination of mutation sites and functional domains, wherein the combination of mutation sites and functional domains includes thermostable mutation sites, low Kd mutation sites, exonuclease-deficient sites and DNA binding domains.

In an embodiment of the invention, the engineered DNA polymerase includes an engineered Phi29 DNA polymerase.

In an embodiment of the invention, the engineered Phi29 DNA polymerase includes mutations Y224K, E239G, V250I, L253A, E375Y, A437G, A484E, E508R, D510K, K512Y, E515Q and D570M.

In an embodiment of the invention, the thermostable mutation sites include M8R, V51A, M97T, G197D and E221K.

In an embodiment of the invention, the low Kd mutation sites include E375 mutated to A or S or E379 mutated to S.

In an embodiment of the invention, the exonuclease-deficient sites include K143 mutated to D, A or S, or Y148 mutated to L.

In an embodiment of the invention, the DNA binding domains include 10his-sso7d or HhH2.

Based on the above, the invention provides an engineered DNA polymerase with increased property for single molecule sequencing by combining the DNA binding domain and mutation sites related to lower exonuclease activity, higher affinity for modified dNTPs and thermostability. In an embodiment of this invention, a modified DNA polymerase (Phi29_Y224K_E239G_V250I_L253A_E375Y_A437G_A484E_E508R_D510K_K512Y_E515Q_D570M+M8R_V51A_M97T_G197D_E221K+Y148L+10his-sso7d) is provided with higher accuracy and longer read-length.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

Figure 1:
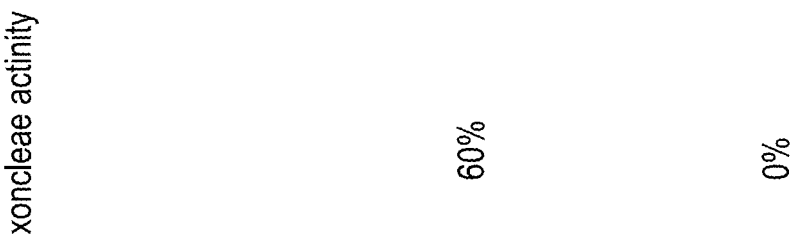
FIG. 1 shows the experimental result of the exonuclease activity assay.

The invention provides an engineered DNA polymerase, with increased property for single molecule sequencing compared to a wild-type DNA polymerase, including a combination of mutation sites and functional domains, wherein the combination of mutation sites and functional domains includes thermostable mutation sites, low Kd mutation sites, exonuclease-deficient sites and DNA binding domains. In the following, the terms used in the specification are defined first.

The term "nucleic acid" or "polynucleotide" encompasses any physical string of monomer units that can be corresponded to a string of nucleotides, including a polymer of nucleotides (e.g., a typical DNA or RNA polymer), PNAs, modified oligonucleotides (e.g., oligonucleotides comprising nucleotides that are not typical to biological RNA or DNA, such as 2'-O-methylated oligonucleotides), and the like. A nucleic acid can be e.g., single-stranded or double-stranded. Unless otherwise indicated, a particular nucleic acid sequence of this invention encompasses complementary sequences, in addition to the sequence explicitly indicated.

A "polypeptide" is a polymer comprising two or more amino acid residues (e.g., a peptide or a protein). The polymer can additionally comprise non-amino acid elements such as labels, quenchers, blocking groups, or the like and can optionally comprise modifications such as glycosylation, biotinylation, or the like. The amino acid residues of the polypeptide can be natural or non-natural and can be unsubstituted, unmodified, substituted or modified.

An "amino acid sequence" is a polymer of amino acid residues (a protein, polypeptide, etc.) or a character string representing an amino acid polymer, depending on context.

A "polynucleotide sequence" or "nucleotide sequence" is a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

The term "engineered" indicates that the material (e.g., a nucleic acid or a protein) has been artificially or synthetically (non-naturally) altered by human intervention. The alteration can be performed on the material within, or removed from, its natural environment or state. For example, an "engineered nucleic acid" is one that is made by recombining nucleic acids, e.g., during cloning, DNA shuffling or other procedures, or by chemical or other mutagenesis.

In an embodiment of the invention, the engineered DNA polymerase includes an engineered Phi29 DNA polymerase. However, the invention is not limited thereto, and other DNA polymerase (ex: M2Y, B103, GA-1) or their recombinant mutants can also be used as backbone to be further engineered with the add-on functions. The engineered Phi29 DNA polymerase is a bacteriophage phi29 DNA polymerase, which is a monomeric enzyme of 66 kDa, a protein-primed DNA-dependent replicase belonging to the eukaryotic-type family of DNA polymerases (family B). Like other DNA polymerases, it accomplishes DNA synthesis by adding nucleotides to the 3'-OH group of growing DNA chain. It contains AN exonuclease domain that catalyzes $3' \rightarrow 5'$ exonucleolysis of mismatched nucleotides. This proofreading feature enhances replication fidelity 102-fold.

In an embodiment of the invention, the combination of functional mutation sites and domain in Phi29 DNA polymerase (Table 1) is tested to further enhance the property of DNA polymerase for single molecule sequencing with higher performance.

TABLE 1

Amino acid sequences of exemplary recombinant Phi29
polymerases including C-terminal exogenous features.
Amino acid sequences of exemplary recombinant
Phi29 polymerases including C-terminal features.

| SEQ ID NO | Amino acid sequence |
|---|---|
| 1. tsH034'<br>Phi29.BtagV7.His6.M8R_V51A_M97T_<br>K143D_G197D_E221K_Y224K_E239G_<br>V250I_L253A_E375Y_A437G_A484E_<br>E508R_D510K_K512Y_E515Q_D570M.<br>GGGSGGGSGGGSG.His10.sso7d | MGSSSSGLNDIFEAQKIEWHEGASSHHHHH<br>HSSGLVPRGSHMKHMPRKRYSCDFETTTKV<br>EDCRVWAYGYMNIEDHSEYKIGNSLDEFMA<br>WALKVQADLYFHNLKFDGAFIINWLERNGF<br>KWSADGLPNTYNTIISRTGQWYMIDICLGY<br>KGKRKIHTVIYDSLKKLPFPVKKIAKDFKL<br>TVLDGDIDYHKERPVGYKITPEEYAYIKND<br>IQIIAEALLIQFKQGLDRMTAGSDSLKDFK<br>DIITTKKFKKVFPTLSLGLDKKVRKAYRGG<br>FTWLNDRFKGKEIGEGMVFDINSAYPAQMY<br>SRLLPYGEPIVFEGKYVWDEDYPLHIQHIR<br>CEFELKEGYIPTIQIKRSRFYKGNEYLKSS<br>GGEIADLWLSNVDLELMKEHYDLYNVEYIS<br>GLKFKATTGLFKDFIDKWTYIKTTSYGAIK<br>QLAKLMLNSLYGKFASNPDVTGKVPYLKEN<br>GALGFRLGEEETKDPVYTPMGVFITAWGRY<br>TTITAAQACYDRIIYCDTDSIHLTGTEIPD<br>VIKDIVDPKKLGYWEHESTFKRAKYLRQKT<br>YIQDIYMKRVKGYLVQGSPDDYTDIKFSVK<br>CAGMTDKIKKEVTFENFKVGFSRKMKPKPV<br>QVPGGVVLVDMTFTIKGGGSGGGSGGGSGH<br>HHHHHHHHHGTGSGAATVKFKYKGEEKEVD<br>ISKIKKVWRVGKMISFTYDEGGGKTGRGAV<br>SEKDAPKELLQMLEKQKK |
| 2. tsH039'<br>Phi29.BtagV7.His6.M8R_V51A_M97T_<br>Y148L_G197D_E221K_Y224K_E239G_<br>V250I_L253A_E375Y_A437G_A484E_<br>E508R_D510K_K512Y_E515Q_D570M.<br>GGGSGGGSGGGSG.His10.sso7d | MGSSSSGLNDIFEAQKIEWHEGASSHHHHH<br>HSSGLVPRGSHMKHMPRKRYSCDFETTTKV<br>EDCRVWAYGYMNIEDHSEYKIGNSLDEFMA<br>WALKVQADLYFHNLKFDGAFIINWLERNGF<br>KWSADGLPNTYNTIISRTGQWYMIDICLGY<br>KGKRKIHTVIYDSLKKLPFPVKKIAKDFKL<br>TVLKGDIDLHKERPVGYKITPEEYAYIKND<br>IQIIAEALLIQFKQGLDRMTAGSDSLKDFK<br>DIITTKKFKKVFPTLSLGLDKKVRKAYRGG<br>FTWLNDRFKGKEIGEGMVFDINSAYPAQMY<br>SRLLPYGEPIVFEGKYVWDEDYPLHIQHIR<br>CEFELKEGYIPTIQIKRSRFYKGNEYLKSS<br>GGEIADLWLSNVDLELMKEHYDLYNVEYIS<br>GLKFKATTGLFKDFIDKWTYIKTTSYGAIK<br>QLAKLMLNSLYGKFASNPDVTGKVPYLKEN<br>GALGFRLGEEETKDPVYTPMGVFITAWGRY<br>TTITAAQACYDRIIYCDTDSIHLTGTEIPD<br>VIKDIVDPKKLGYWEHESTFKRAKYLRQKT<br>YIQDIYMKRVKGYLVQGSPDDYTDIKFSVK<br>CAGMTDKIKKEVTFENFKVGFSRKMKPKPV<br>QVPGGVVLVDMTFTIKGGGSGGGSGGGSGH<br>HHHHHHHHHGTGSGAATVKFKYKGEEKEVD |

TABLE 1-continued

Amino acid sequences of exemplary recombinant Phi29
polymerases including C-terminal exogenous features.
Amino acid sequences of exemplary recombinant
Phi29 polymerases including C-terminal features.

| SEQ ID NO | Amino acid sequence |
|---|---|
| | ISKIKKVWRVGKMISFTYDEGGGKTGRGAV<br>SEKDAPKELLQMLEKQKK |
| 3. tsH041'<br>Phi29.BtagV7.His6.M8R_V51A_M97T_<br>K143A_G197D_E221K_Y224K_E239G_<br>V250I_L253A_E375Y_A437G_A484E_<br>E508R_D510K_K512Y_E515Q_D570M.<br>GGGSGGGSGGGSG.His10.sso7d | MGSSSSGLNDIFEAQKIEWHEGASSHHHHH<br>HSSGLVPRGSHMKHMPRKRYSCDFETTTKV<br>EDCRVWAYGYMNIEDHSEYKIGNSLDEFMA<br>WALKVQADLYFHNLKFDGAFIINWLERNGF<br>KWSADGLPNTYNTIISRTGQWYMIDICLGY<br>KGKRKIHTVIYDSLKKLPFPVKKIAKDFKL<br>TVLAGDIDYHKERPVGYKITPEEYAYIKND<br>IQIIAEALLIQFKQGLDRMTAGSDSLKDFK<br>DIITTKKFKKVFPTLSLGLDKKVRKAYRGG<br>FTWLNDRFKGKEIGEGMVFDINSAYPAQMY<br>SRLLPYGEPIVFEGKYVWDEDYPLHIQHIR<br>CEFELKEGYIPTIQIKRSRFYKGNEYLKSS<br>GGEIADLWLSNVDLELMKEHYDLYNVEYIS<br>GLKFKATTGLFKDFIDKWTYIKTTSYGAIK<br>QLAKLMLNSLYGKFASNPDVTGKVPYLKEN<br>GALGFRLGEEETKDPVYTPMGVFITAWGRY<br>TTITAAQACYDRIIYCDTDSIHLTGTEIPD<br>VIKDIVDPKKLGYWEHESTFKRAKYLRQKT<br>YIQDIYMKRVKGYLVQGSPDDYTDIKFSVK<br>CAGMTDKIKKEVTFENFKVGFSRKMKPKPV<br>QVPGGVVLVDMTFTIKGGGSGGGSGGGSGH<br>HHHHHHHHHGTGSGAATVKFKYKGEEKEVD<br>ISKIKKVWRVGKMISFTYDEGGGKTGRGAV<br>SEKDAPKELLQMLEKQKK |
| 4. tsH042'<br>Phi29.BtagV7.His6.M8R_V51A_M97T_<br>K143S_G197D_E221K_Y224K_E239G_<br>V250I_L253A_E375Y_A437G_A484E_<br>E508R_D510K_K512Y_E515Q_D570M.<br>GGGSGGGSGGGSG.His10.sso7d | MGSSSSGLNDIFEAQKIEWHEGASSHHHHH<br>HSSGLVPRGSHMKHMPRKRYSCDFETTTKV<br>EDCRVWAYGYMNIEDHSEYKIGNSLDEFMA<br>WALKVQADLYFHNLKFDGAFIINWLERNGF<br>KWSADGLPNTYNTIISRTGQWYMIDICLGY<br>KGKRKIHTVIYDSLKKLPFPVKKIAKDFKL<br>TVLSGDIDYHKERPVGYKITPEEYAYIKND<br>IQIIAEALLIQFKQGLDRMTAGSDSLKDFK<br>DIITTKKFKKVFPTLSLGLDKKVRKAYRGG<br>FTWLNDRFKGKEIGEGMVFDINSAYPAQMY<br>SRLLPYGEPIVFEGKYVWDEDYPLHIQHIR<br>CEFELKEGYIPTIQIKRSRFYKGNEYLKSS<br>GGEIADLWLSNVDLELMKEHYDLYNVEYIS<br>GLKFKATTGLFKDFIDKWTYIKTTSYGAIK<br>QLAKLMLNSLYGKFASNPDVTGKVPYLKEN<br>GALGFRLGEEETKDPVYTPMGVFITAWGRY<br>TTITAAQACYDRIIYCDTDSIHLTGTEIPD<br>VIKDIVDPKKLGYWEHESTFKRAKYLRQKT<br>YIQDIYMKRVKGYLVQGSPDDYTDIKFSVK<br>CAGMTDKIKKEVTFENFKVGFSRKMKPKPV<br>QVPGGVVLVDMTFTIKGGGSGGGSGGGSGH<br>HHHHHHHHHGTGSGAATVKFKYKGEEKEVD<br>ISKIKKVWRVGKMISFTYDEGGGKTGRGAV<br>SEKDAPKELLQMLEKQKK |

1. Screen Exonuclease Deficient Mutation Site

Previously, a modified Phi29 DNA polymerase G05 with high affinity for modified nucleotides analog has been constructed. The G05 mutant contains the following mutation sites 5 M8R_V51A_M97T_G197D_E221K_L253A_ E375Y_L384N_A484E_K512Y. However, G05 mutant shows high exonuclease activity (65%), which might affect the accuracy of single-molecule sequencing. The G05 mutant can be used as a backbone to screen mutation sites which are related to exonuclease activity. The data shows the mutants with E14I, K143D/R, Y148L/M, D169N and F211A/H mutation sites demonstrates lower exonuclease activity than G05 with similar polymerization activity in RCA analysis (Table 2). These mutation sites can be used to reduce the exonuclease activity of DNA polymerase for single molecule sequencing with higher sequencing accuracy.

Table 2 demonstrates the screening of G05 derived mutants with mutation sites related to exonuclease deficient. The G05 mutant (M8R_V51A_M97T_G197D_E221K_ L253A_E375Y_L384N_A484E_K512Y) which shows high exonuclease activity (65%) is suitable to screen the exonuclease deficient sites. RCA (rolling circle amplification) analysis and exonuclease activity assay are used to screen the mutants. RCA analysis result are represented with "+" sign, the more "+" sign indicates the activity is higher. "++++" indicates the DNA polymerase shows higher activity than G05. "+++" indicates the DNA polymerase shows similar activity to G05. "++" and "+" indicate the DNA polymerase shows lower activity than G05. The mutant recited in bold shows the mutation sites can reduced the exonuclease activity while maintaining the polymerization activity at the same time.

TABLE 2

| mutant | mutation site | RCA analysis | exonuclease activity |
|---|---|---|---|
| G054 | D12A | ND | NA |
| G055 | D12M | ND | NA |
| G056 | D12N | ND | 6.6% |
| G057 | D12R | ND | 7.0% |
| G058 | E14A | ND | 6.5% |
| G059 | E14I | +++ | 52.6% |
| G060 | E14Q | ND | 6.0% |
| G061 | T15I | ND | NA |
| G062 | H61A | ND | NA |
| G063 | G61D | ND | NA |
| G064 | H61K | ND | NA |
| G065 | N62S | ND | NA |
| G066 | F65S | ND | NA |
| G067 | D66A | ND | 0.0% |
| G068 | D66K | ND | 0.0% |
| G069 | D66M | ND | 0.0% |
| G070 | D66N | ++ | 0.0% |
| G071 | D66Q | ++ | 0.0% |
| G072 | D66R | ND | 0.0% |
| G073 | S122T | ND | NA |
| G074 | L123N | ND | NA |
| G075 | K143D | +++ | 37.5% |
| G076 | K143R | ++ | 8.4% |
| G077 | D145A | +++ | 68.6% |
| G078 | Y148A | +++ | 3.4% |
| G079 | Y148C | +++ | 11.8% |
| G080 | Y148D | +++ | 4.4% |
| G081 | Y148E | + | 0.0% |
| G082 | Y148F | ++ | 6.1% |
| G083 | Y148G | +++ | 7.8% |
| G084 | Y148H | +++ | 21.1% |
| G085 | Y148I | +++ | 48.4% |
| G087 | Y148L | +++ | 34.5% |
| G088 | Y148M | +++ | 8.7% |
| G089 | Y148N | +++ | 0.0% |
| G090 | Y148P | +++ | 0.0% |
| G091 | Y148Q | + | 0.0% |
| G092 | Y148R | + | 2.0% |
| G093 | Y148S | ++ | 3.4% |
| G094 | Y148T | ++ | 11.0% |
| G095 | Y148V | + | 7.5% |
| G096 | Y148W | + | 44.6% |
| G097 | H149M | +++ | 30.6% |
| G098 | D169A | +++ | NA |
| G099 | D169N | +++ | 6.6% |
| G100 | I179A | ++ | 51.2% |
| G101 | I179H | ND | 47.2% |
| G102 | I179W | ND | 53.4% |
| G103 | T189A | ND | 19.3% |
| G104 | T189S | ++ | 40.9% |
| G105 | F198A | ND | NA |
| G106 | F196H | ++ | NA |
| G107 | F198W | ND | NA |
| G108 | F211A | ++ | 39.0% |
| G109 | F211H | ++ | 35.0% |
| G110 | F211W | ND | NA |
| G111 | P255A | ND | NA |
| G112 | P255H | ND | NA |
| G113 | P255W | ND | NA |
| G114 | Y259A | ND | 63.9% |
| G115 | Y259W | ND | NA |
| G116 | F360A | ND | NA |
| G117 | F360H | ND | NA |
| G118 | F360W | ND | NA |
| G119 | F363A | ND | NA |
| G120 | F363H | ND | NA |
| G121 | F363W | ND | NA |
| G122 | I370A | ND | NA |
| G123 | I370W | ND | NA |
| G124 | K371A | ND | NA |
| G125 | K371W | ND | NA |

TABLE 2-continued

| mutant | mutation site | RCA analysis | exonuclease activity |
|---|---|---|---|
| G126 | I378A | ND | 49.3% |
| G127 | I378H | ++ | 57.6% |
| G128 | L381A | ++ | 54.7% |
| G129 | L381H | ND | NA |
| G130 | L381W | ND | NA |
| G131 | K383A | ND | 62.7% |
| G132 | K383N | ND | 57.7% |
| G133 | L389A | ND | NA |
| G134 | L389H | ND | NA |
| G135 | L389W | ND | NA |
| G136 | F393A | ND | NA |
| G137 | F393H | ND | NA |
| G138 | F393W | ND | NA |
| G139 | I433H | ND | NA |
| G140 | I433W | ND | NA |
| G141 | I433A | ND | NA |

2. Engineered the DNA Polymerase with Lower Exonuclease Activity and Higher Affinity for Nucleotides Analog to Enhance the Sequencing Performance According to U.S. Pat. No. 9,873,911B2, a series of modified Phi29 DNA polymerase have been shown to use protein shield nucleotides analog as substrates to perform single molecule sequencing. Among these modified Phi29 DNA polymerases, a mutant named H04 which contains mutation sites Y224K_E239G_V250I_L253A_E375Y_A437G_A484E_E508R_D510K_K512Y_E515Q_D570M showing higher activity is selected as a backbone to be further engineered with functional domains or mutation sites for better performance in single molecule real time sequencing.

From protein structural analysis, the sites related to higher substrate affinity (F211A, T372A, E375A/S, K379A/S, N387H/Q/Y, K478A/S, K512A, V514A and K539A/S) are selected to add on the H04 DNA polymerase. Also, the exonuclease activity sites (E14I/Q, K143D/R, H149M, D169Q, Y148L/M, T189A/S) screened by G05 mutagenesis study are added on the H04 DNA polymerase. As shown in Table 3, the H019, H020 and H022 mutants with substrate affinity (low Kd) related mutation site (E375A, E375S, E379S) show higher activity (++++) than the H04 DNA polymerase in RCA (rolling circle amplification on coverslip) analysis. The H034, H041, H042 and H039 mutants with nuclease-deficient related mutation sites (K143D, K143A, K143S, Y148L) show similar activity to H04 DNA polymerase but is expected to have better sequencing quality, since the exonuclease activity is reduced to avoid interference in single molecule real time sequencing reaction.

TABLE 3

Low Kd mutation sites and exonuclease deficient sites was added on H04 mutant to enhance the property for single molecule sequencing. The mutant recited in bold showed the substrate affinity was increased or exonuclease activity was reduced with similar polymerization activity.

| Domain | mutant | mutation site | RCA analysis | exo |
|---|---|---|---|---|
| Palm | H038 | F211A | ND | NA |
| Fingers | H018 | T372A | + | NA |
| Fingers | H019 | E375A | ++++ | 39.09% |
| Fingers | H020 | E375S | ++++ | 56.52% |
| Fingers | H021 | K379A | +++ | 53.64% |
| Fingers | H022 | K379S | ++++ | 62.25% |

TABLE 3-continued

Low Kd mutation sites and exonuclease deficient sites was
added on H04 mutant to enhance the property for single
molecule sequencing. The mutant recited in bold showed
the substrate affinity was increased or exonuclease activity
was reduced with similar polymerization activity.

| Domain | mutant | mutation site | RCA analysis | exo |
|---|---|---|---|---|
| Fingers | H023 | N387H | ND | 44.42% |
| Fingers | H024 | N387Q | ND | 21.93% |
| Fingers | H025 | N387Y | ND | 24.96% |
| Palm | H026 | K478A | +++ | 55.95% |
| Palm | H027 | K478S | +++ | 46.76% |
| Palm | H028 | K512A | +++ | NA |
| Palm | H029 | V514A | + | 34.88% |
| Thumb | H030 | K539A | +++ | NA |
| Thumb | H031 | K539S | ++ | NA |
| Exo | H032 | E14I | ND | NA |
| Exo | H033 | E14Q | ND | NA |
| Exo | H034 | K143D | +++ | 1.80% |
| Exo | H035 | K143R | ++ | 2.07% |
| Exo | H041 | K143A | +++ | NA |
| Exo | H042 | K143S | ++++ | NA |
| Exo | H036 | H149M | ++ | NA |
| Exo | H037 | D169N | ND | 0% |
| Palm | H038 | F211A | ND | NA |
| Exo | H039 | Y148L | +++ | NA |
| Exo | H040 | Y148M | ++ | NA |
| | H004 | | +++ | 38% |

3. Improve DNA Binding Stability

The principle of single-molecule sequencing mainly relies on the detection of signals generated by DNA polymerase incorporating nucleotides during DNA synthesis. In particular, the DNA template for single molecule sequencing is in a very low concentration, and it is necessary for the binding affinity between DNA template and DNA polymerase to be enhanced to prevent the dissociation during sequencing process. In addition, the fluorescence labeled dNTPs used in single molecule sequencing is in a very low concentration (20 nM). In order to obtain longer read length, the DNA polymerase is required to stably bind with very low concentration of DNA template and perform DNA synthesis with low concentration of fluorescence labeled dNTPs during the single molecule sequencing process. The DNA binding domain 10his, sso7d and HhH2 have been shown to increase the DNA binding stability and processivity of DNA polymerase in many studies. Hence, the DNA binding domain sso7d is fused to the c-terminal end of DNA polymerase. To analyzed the activity of mutant protein with sso7d, the modified dNTPs conversion rate analysis is performed with low concentration (100 pM) of DNA template and fluorescence labeled dNTPs (20 nM). As shown in Table 4, DNA polymerase fused with 10his-sso7d DNA binding domain (mutant name end with a symbol') shows higher activity than those without the 10his-sso7d DNA binding domain in the conversion rate analysis. (Table 4)

TABLE 4

Modified DNA polymerase fused with DNA binding
domain(10his-sso7d) shows higher activity
than those without DNA binding domain.

| mutant | mutation site | Conversion rate of modified dNTPs | mutant (+sso7d) | Conversion rate of modified dNTPs |
|---|---|---|---|---|
| H004 | | 48.41% | H004' | 69.35% |
| H041 | K143A | 24.49% | H041' | 68.59% |
| H042 | K143S | 34.14% | H042' | 60.10% |

4. Improve Protein Thermostability

Since the single-molecule sequencing relies on the DNA polymerase to generate fluorescent signals by laser excitation during DNA synthesis, the DNA polymerase must have the ability to resist photo damage for a long time. Therefore, the protein stability is very important for single-molecule sequencing. It has been reported that M8R, V51A, M97T, G197D, E221K mutations can increase the thermostability of Phi29 DNA polymerase. To test whether these sites can also increase the thermostability of H04 series mutant, M8R, V51A, M97T, G197D, E221K mutation sites are added into the H04, H019, H020 and H022. The thermostable mutants are named with "ts" at the beginning of names. As shown in Table 5, the mutants with thermostable mutation sites (M8R, V51A, M97T, G197D, E221K) show higher activity than that without these mutation sites.

TABLE 5

Modified DNA polymerase with thermostable mutation sites show
higher activity than those without thermostable mutation sites.

| mutant | mutation site | Conversion rate of modified dNTPs | mutant (+ts) | Conversion rate of modified dNTPs |
|---|---|---|---|---|
| H004 | — | 19.9% | tsH004 | 56.6% |
| H019 | E375A | 22.2% | tsH019 | 60.4% |
| H020 | E375S | 46.2% | tsH020 | 45.8% |
| H022 | K379S | 32.5% | tsH022 | 50.3% |
| H034 | K143D | 5.4% | tsH034 | 4.7% |

5. Single Molecule Sequencing Reaction of the Modified Phi29 DNA Polymerase with Combination of Multiple Functional Mutation Sites and Domain.

As the shown in the above data, low Kd mutation sites (E375A, E375S, E379S), exonuclease-deficient sites (K143D, K143A, K143S, Y148L), DNA binding domains (10his-sso7d) and thermostable mutation sites (M8R, V51A, M97T, G197D, E221K) enhance the activity of Phi29 DNA polymerase H04. To further evaluate the pros and cons of these modified DNA polymerase, the single molecule real-time sequencing system is employed to analyze the sequencing performance (accuracy, read length) of these modified DNA polymerases. As shown in Table 6, single molecule sequencing using tsH039' DNA polymerase (Phi29 Y224K_E239G_V250I_L253A_E375Y_A437G_A484E_E508R_D510K_K512Y_E515Q_D570M+ M8R_V51A_M97T_G197D_E221K+Y148L+10his-sso7d) presents higher accuracy (identity) and longer read-length than the original tsH004 or tsH004' DNA polymerase (Phi29 Y224K_E239G_V250I_L253A_E375Y_A437G_A484E_E508R_D510K_K512Y_E515Q_D570M). According to the further analysis of the error rate of the sequence data, it is found that the insertion error rate of tsH039', tsH034' and tsH042' is significantly lower than that of H004, presumably because Y148L and K143D/S mutation sites reduce the exonuclease activity, thus prevent the DNA polymerase from cut back and re-synthesized DNA which might generate signal as insertion error during the single-molecule sequencing process, particularly, when the reaction condition is of low concentration of dNTPs. The read length of tsH034' and tsH042' is slightly shorter than the tsH004' may be due to polymerization activity decrease by K143D/S mutation sites (as shown in Table 4 and Table 5, the dNTPs conversion rate of H034 and H042 is lower than H004). The tsH004' mutant shows longer read length (template aligned length) and accuracy than tsH004 may be due to the binding stability contributed by the DNA binding domain sso7d.

The K143 and Y148 sites can also be mutated to other amino acids for compatibility with different DNA polymerases as backbones. In addition to H004 as backbone, other DNA polymerase ex: M2Y, B103, GA-1 and their recombinant mutants can also be used as backbone to be further engineered with the add-on functions.

3. Rolling Circle Amplification Assay on Coverslip

Figure 2:
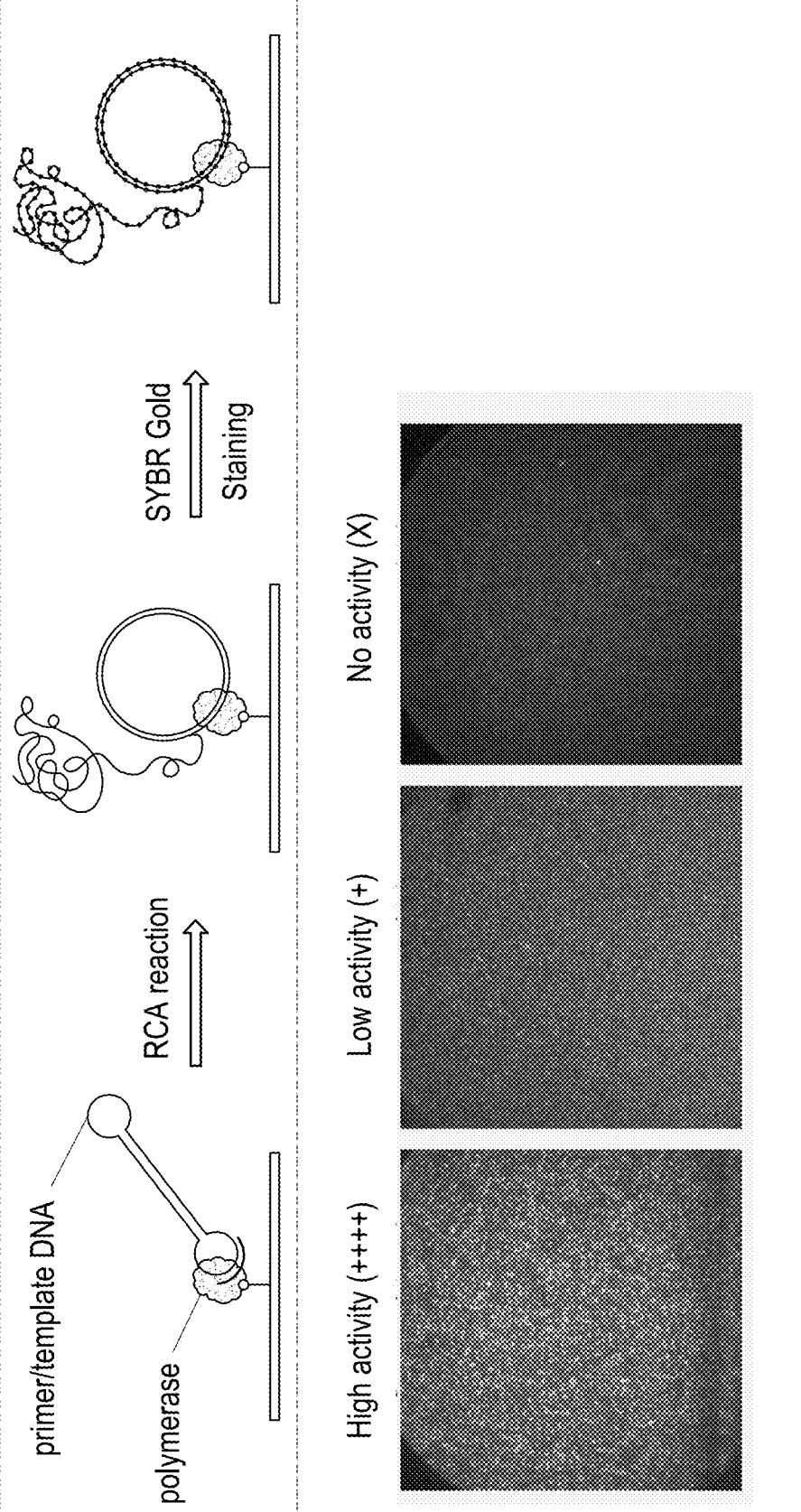
FIG. 2 shows the experimental result of the rolling circle amplification assay on coverslip.

The rolling circle amplification analysis uses circular DNA as a template to analyze the activity of mutant protein for DNA polymerization. The DNA produced by RCA reaction is stained with SYBR® Gold and observed under a microscope. If the activity of the mutant is good, the microscope view will show a relatively more staining spots, and the staining spots are also larger; otherwise, if the number of staining spots is few and size is small, it indicates the activity of mutant protein is low (as shown in FIG. 2).

4. Modified dNTPs Conversion Rate Analysis

The conversion rate analysis method uses HPLC instrument to analyze the ratio of fluorescent label dNTPs used by DNA polymerase in reaction condition of very low concentration of DNA template (100 pM) and modified dNTPs (20

TABLE 6

Single molecule sequencing analysis of modified Phi29 DNA polymerase. The tsH039' (recited in bold) shows better performance in single molecule real time sequencing than tsH004'.

| | | | Top20 Average | | | | |
|---|---|---|---|---|---|---|---|
| | Mutation | Raw Read Base | Template Aligned Length | Identity | Error rate_Insertion | Error rate_Deletion | Error rate_Substitution |
| tsH004 | M8R_V51A_M97T_K143D_G197D_E221K | 390.4 | 326.7 | 75.2% | 14.1% | 5.0% | 5.7% |
| tsH004' | M8R_V51A_M97T_K143D_G197D_E221K + sso7d | 399.9 | 358.6 | 77.2% | 10.6% | 5.5% | 6.7% |
| tsH034' | M8R_V51A_M97T_K143D_G197D_E221K + K143D + sso7d | 312.0 | 281.6 | 77.3% | 7.4% | 8.3% | 7.1% |
| tsH039' | M8R_V51A_M97T_K143D_G197D_E221K + Y148L + sso7d | 428.0 | 436.0 | 79.6% | 5.8% | 8.4% | 6.2% |
| tsH042' | M8R_V51A_M97T_K143D_G197D_E221K + K143S + sso7d | 348.3 | 341.6 | 80.6% | 5.2% | 8.0% | 6.2% |

Materials and Methods

1. Making and Isolating Recombinant Polymerases

In General, the DNA Sequence Encoding a Polymerase of the Invention is Made by PCR, cloning, and recombination method. The DNA sequence is codon optimized and cloned into pET28a expression vector. To expressed the recombinant protein, the expression vector is transformed into BL21(DE3) host cells and induced by IPTG for protein expression. The mutant protein is purified by Ni-chromatography with high salt (1.5 M KCl) to eliminate DNA contamination. After the Ni-chromatography purification, size exclusion chromatography was further employed to increase the purity of mutant DNA polymerase. For performing single molecule real-time sequencing reaction, the mutant protein is also expressed as biotinylated form and bound with streptavidin as complex and purified by size exclusion chromatography for immobilization on coverslip.

2. Exonuclease Activity Assay

The exonuclease activity analysis method is calculated by using the hydrolysis ratio of the Primer. The fluorescent label primer is incubated with the mutant protein for 2 minutes and the reaction product is analyzed by ABI3500 capillary sequencer. The residual amount of the primer after hydrolysis by the mutant protein is measured. By compared to the initial amount of primer, the amount of hydrolyzed primer can be calculated. As a result, the percentage of exonuclease activity can be calculated by dividing the amount of hydrolyzed primer to the amount of input primer. As shown in FIG. 1, the exo+ mutant protein hydrolyzes the primer and gets a high percentage of exonuclease activity while the exo-mutant protein doesn't hydrolyzed the primer and shows no exonuclease activity.

nM). After calculation, the conversion rate of fluorescent label dNTPs represents the activity of DNA polymerase when using the modified dNTPs. The reaction conditions of this experiment are as follows: Primer/Template: 100 pM, mutant protein: 300 pM, 5'-dN6P-532: 20 nM, Mg(OAc)$_2$: 5 mM, DTT: 10 mM; reaction volume 10 ul; reaction time: 30 minute.

5. Single Molecule Real Time Sequence Reaction

The single molecule real time sequencing analysis employs the optical image system (contain TIRF microscopy, laser, filter lens and image recorder) to record the sequencing reaction. The experimental procedure is as follows: 1. Mutant DNA polymerase is bound with the circular DNA template to form a complex; 2. DNA template/Primer/DNA polymerase ternary complex is immobilized on a PEG-biotin coverslip by streptavidin/biotin chemistry; 3. Reaction buffer with fluorescent label dNTPs is added on the coverslip to start the sequencing reaction; and 4. Realtime sequencing reaction is recorded by the imaging system for 30 minutes.

6. Base Calling Algorism and Sequence Analysis

The base calling algorism is developed to process the movie file generated by the optical image system into DNA sequence. In briefly, the base calling algorism analyzes the pulse signal generated when the fluorescent labeled dNTP incorporated into the newly synthesized DNA by single DNA polymerase and converts the pulsed signal into ATCG sequence data. By compared to the reference sequence, the sequence accuracy (identity) can be delivered. As shown in Table 6, the average accuracy (identity) of a mutant DNA polymerase is calculated by the averaging the top 20 sequencing data with the highest accuracy (identity). The sequencing error rate is differentiated as insertion, deletion and substitution.

Based on the above, the invention provides an engineered DNA polymerase, with increased property for single molecule sequencing compared to a wild-type DNA polymerase, including a combination of mutation sites and functional domains, wherein the combination of mutation sites and functional domains includes thermostable mutation sites, low Kd mutation sites, exonuclease-deficient sites and DNA binding domains. The invention combines the DNA binding domain and mutation sites related to lower exonuclease activity, higher affinity for modified dNTPs and thermostability, so the engineered DNA polymerase of the invention has higher accuracy and longer read-length.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. An engineered DNA polymerase, with increased property for single molecule sequencing compared to a wild-type DNA polymerase, comprising a combination of mutation sites and functional domains, wherein the combination of mutation sites and functional domains includes thermostable mutation sites, low Kd mutation sites, exonuclease-deficient sites and DNA binding domains, wherein the engineered DNA polymerase comprises the amino acid sequences of SEQ ID NOs: 1-4.

* * * * *